(12) United States Patent
Greenhalgh

(10) Patent No.: US 9,456,830 B2
(45) Date of Patent: *Oct. 4, 2016

(54) BONE GRAFT DELIVERY SYSTEM AND METHOD FOR USING SAME

(71) Applicant: Surgical Device Exchange, LLC, Boca Raton, FL (US)

(72) Inventor: Travis Greenhalgh, Boca Raton, FL (US)

(73) Assignee: Surgical Device Exchange, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/593,489

(22) Filed: Jan. 9, 2015

(65) Prior Publication Data

US 2015/0190148 A1 Jul. 9, 2015

Related U.S. Application Data

(63) Continuation of application No. 13/485,641, filed on May 31, 2012, now Pat. No. 8,932,295.

(60) Provisional application No. 61/492,316, filed on Jun. 1, 2011.

(51) Int. Cl.
| | |
|---|---|
| *A61B 17/16* | (2006.01) |
| *A61F 2/28* | (2006.01) |
| *A61F 2/46* | (2006.01) |

(52) U.S. Cl.
CPC ....... *A61B 17/1659* (2013.01); *A61B 17/1635* (2013.01); *A61B 90/39* (2016.02); *A61F 2/28* (2013.01); *A61F 2/4601* (2013.01); *A61B 2090/3966* (2016.02); *A61F 2002/2835* (2013.01)

(58) Field of Classification Search
CPC ...... A61B 17/8816; A61B 19/54; A61F 2/28
USPC ..................................................... 606/92–94
See application file for complete search history.

(56) References Cited

U.S. PATENT DOCUMENTS

| | | | |
|---|---|---|---|
| 2,316,095 A | 4/1943 | Mead | |
| 4,277,184 A | 7/1981 | Solomon | |
| 4,338,925 A * | 7/1982 | Miller | A61B 17/8811 604/61 |
| 5,531,749 A * | 7/1996 | Michelson | A61B 19/00 606/93 |
| 5,733,288 A * | 3/1998 | Allen | A46B 3/08 606/79 |
| 6,439,439 B1 | 8/2002 | Rickard et al. | |
| 6,814,736 B2 | 11/2004 | Reiley et al. | |
| 7,141,054 B2 | 11/2006 | Vandewalle | |
| 7,306,603 B2 | 12/2007 | Boehm, Jr. et al. | |
| 7,513,901 B2 * | 4/2009 | Scifert | A61B 17/8816 606/92 |
| 7,799,033 B2 | 9/2010 | Assell et al. | |
| 7,811,291 B2 | 10/2010 | Liu et al. | |
| 7,887,543 B2 | 2/2011 | Sand et al. | |

(Continued)

*Primary Examiner* — Christopher Beccia
(74) *Attorney, Agent, or Firm* — Knobbe, Martens, Olson & Bear, LLP.

(57) ABSTRACT

A bone graft delivery system can include an elongate tube, a handle having a trigger, and a tip. The trigger is actuated to deliver bone graft material through the tube. The tip has one or more openings to deliver the bone graft material to a desired location and includes a surface suitable to act as a rasp for decorticating bone. A method for delivering bone graft material to a desired surgical location includes providing a bone graft delivery device, positioning the device adjacent the surgical location, decorticating bone, and delivering bone graft material to the surgical location.

17 Claims, 2 Drawing Sheets

(56) References Cited

U.S. PATENT DOCUMENTS

| | | |
|---|---|---|
| 8,308,805 B2 | 11/2012 | Lynn et al. |
| 2004/0024409 A1 | 2/2004 | Sand et al. |
| 2004/0133211 A1* | 7/2004 | Raskin ............... A61B 17/3468 606/92 |
| 2005/0107800 A1* | 5/2005 | Frankel ............. A61B 17/1655 606/92 |
| 2005/0137604 A1 | 6/2005 | Assell et al. |
| 2005/0171549 A1 | 8/2005 | Boehm, Jr. et al. |
| 2005/0203523 A1 | 9/2005 | Wenstrom, Jr. et al. |
| 2006/0293687 A1 | 12/2006 | Bogert |
| 2007/0005072 A1 | 1/2007 | Castillo et al. |
| 2007/0276397 A1 | 11/2007 | Pacheco |
| 2008/0065082 A1* | 3/2008 | Chang ............... A61B 17/1659 606/85 |
| 2008/0125856 A1 | 5/2008 | Perez-Cruet et al. |
| 2008/0300684 A1 | 12/2008 | Shelokov |
| 2009/0216238 A1 | 8/2009 | Stark |
| 2009/0318925 A1 | 12/2009 | Campion et al. |
| 2010/0036381 A1* | 2/2010 | Vanleeuwen ...... A61B 17/1617 606/80 |
| 2010/0057087 A1 | 3/2010 | Cha |
| 2010/0174286 A1 | 7/2010 | Truckai et al. |
| 2010/0179556 A1 | 7/2010 | Scribner |
| 2010/0204702 A1 | 8/2010 | Lechot et al. |
| 2010/0262146 A1 | 10/2010 | Tulkis |
| 2011/0071527 A1* | 3/2011 | Nelson ............... A61B 17/1624 606/85 |
| 2011/0071536 A1 | 3/2011 | Kleiner et al. |
| 2012/0253316 A1 | 10/2012 | Oktavec et al. |
| 2015/0105748 A1 | 4/2015 | McBride et al. |

* cited by examiner

BONE GRAFT DELIVERY SYSTEM AND METHOD FOR USING SAME

CROSS-REFERENCE TO RELATED APPLICATIONS

This application is a continuation of U.S. application Ser. No. 13/485,641, entitled "BONE GRAFT DELIVERY SYSTEM AND METHOD FOR USING SAME," filed May 31, 2012, which claims priority benefit of U.S. Provisional Application No. 61/492,316, entitled "BONE GRAFT DELIVERY SYSTEM AND METHOD FOR USING SAME," filed Jun. 1, 2011, the entirety of each of which is hereby incorporated by reference herein.

BACKGROUND

1. Field

The present application relates to orthopedic surgery in general, and more particularly, to bone graft delivery systems and methods.

2. Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein also provide for bone decortication.

In some embodiments, a bone graft delivery system includes an elongate tube, a handle at a proximal end of the tube configured to be actuated to deliver bone graft material through the tube, and a tip at a distal end of the tube. The handle may include a trigger. The tip includes one or more openings configured to deliver the bone graft material to a desired location and a surface suitable to serve as a rasp for scraping bone.

In some embodiments, a method for delivering bone graft material to a surgical location includes providing a bone graft delivery device comprising an elongate tube and a distal tip having at least one opening for delivering the bone graft material to the surgical location and positioning the device adjacent the surgical location. The method further includes decorticating bone with the distal tip and delivering bone graft material through the tube and out the at least one opening of the tip.

DETAILED DESCRIPTION

Figure 1:
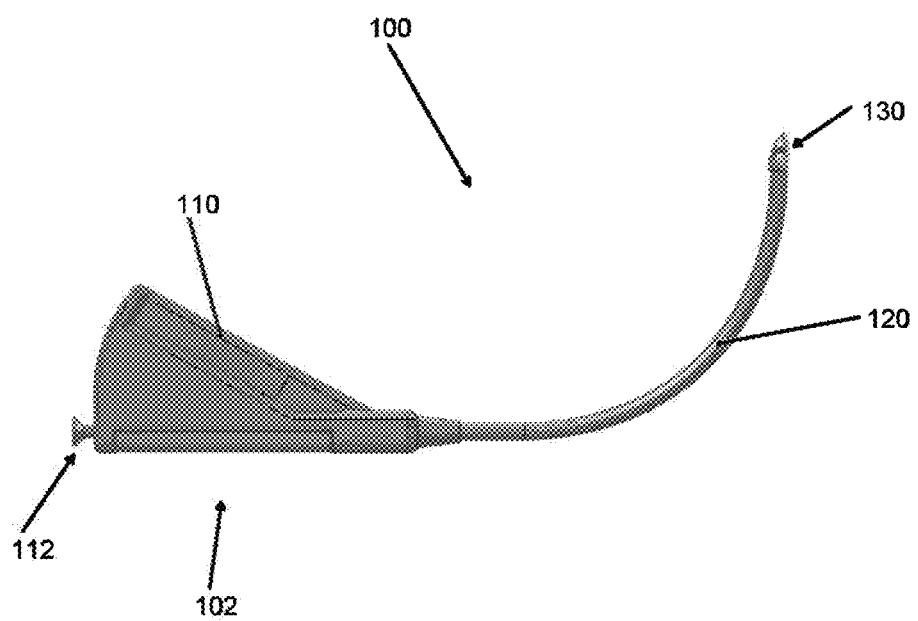
FIG. 1 illustrates a side view of an example embodiment of a bone graft delivery device.
Figure 2:
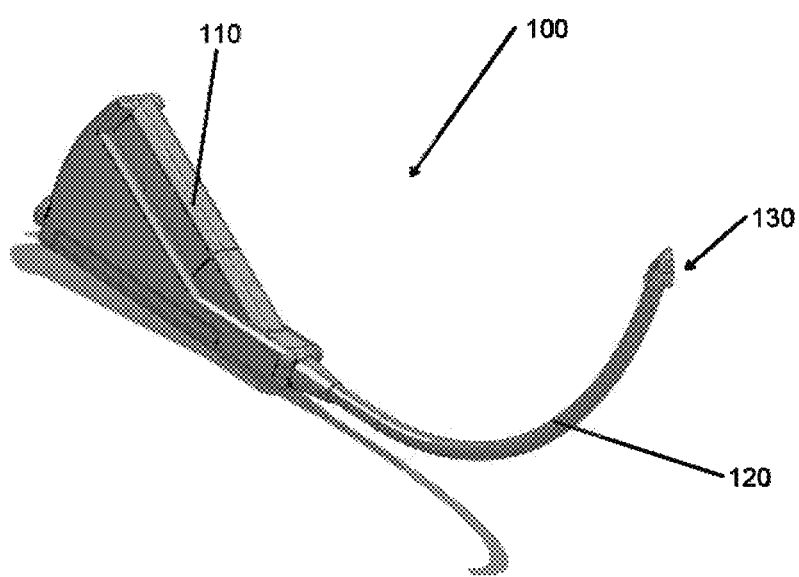
FIG. 2 illustrates a perspective view of the bone graft delivery device of FIG. 1.

As shown in FIGS. 1 and 2, a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or can be supplied to the handle via a cartridge that can be removably coupled to the handle 102. In some embodiments, the device 100 can further include a plunger 112 that is retracted proximally to allow the handle to receive a cartridge or pre-loaded volume of bone graft material.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

As shown in FIGS. 1 and 2, the tube 120 can include a permanent bend or curve that may be useful in positioning the device 100 at a desired location, for example, a space between two spinal discs. Alternatively, the tube 120 may be straight to deliver bone graft material directly into a desired location such as a disc space. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal, and is generally hollow to allow for the passage of bone graft material through the tube 120.

Figure 3:
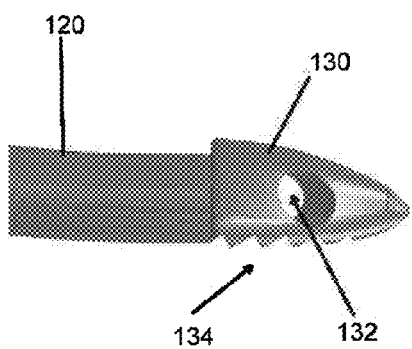
FIGS. 3-5 illustrates various views of a distal tip of the bone graft delivery device of FIGS. 1 and 2.
Figure 4:
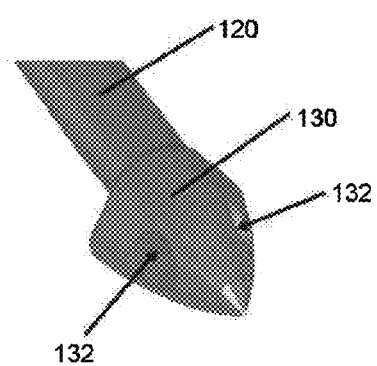
Figure 5:
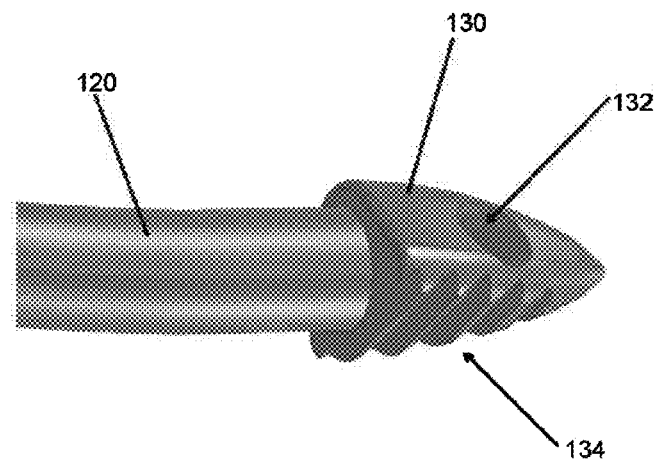

As shown in FIGS. 3-5, a distal end of the tube 120 includes a tip 130. In the illustrated embodiment, the tip 130 is somewhat bullet-shaped with a generally triangular cross-section; however, other shapes and configurations are also possible. In some embodiments, the tip 130 is pointed and/or sharp to dissect or split muscle and tissue as it is advanced through the patient's skin and body to the surgical location. Alternatively, the tip 130 can be blunt to allow for displacement of muscle without risk of cutting of nerves or other tissue. The tip has a single or multiple openings 132 in fluid communication with the tube 120 lumen and configured to deliver the bone graft material from the tube 120 to the desired location.

In some embodiments, at least one side or area of the tip 130 includes a series of jagged edges or other suitable surface 134 configured to serve as a rasp for scraping bone. The rasp may be operated manually or by mechanical, battery powered, electric, pneumatic, or any other means of force to allow for decortication of the area to receive the bone graft material.

The tip 130 may be made of a metallic, radiopaque material to facilitate visualization on, for example, fluoroscopy or x-ray. Alternatively, the tip 130 may be made of another material, for example a durable medical plastic or a composite material, and may include markers to facilitate visualization.

In one embodiment, the device 100 described herein may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, or facet joints, through one of these small incisions. The device described herein is sized to be delivered through a minimally invasive opening made in the patient's skin (e.g., through a skin incision of 4 cm or less), and configured so that the tip can be positioned adjacent a pedicle screw or other desired location. The curvature of the tube 120 can facilitate positioning of the tip 130 at desired spinal locations and allows, for example, insertion of the device 100 through an incision over one vertebra, and positioning of the tip 130 at an adjacent vertebra. Alternatively, the device can be delivered through any desired opening made in the patient's skin (e.g., minimally invasive or open). The jagged edges or other surface 134 on the device can be used to decorticate desired bone locations, causing bleeding of the bone and creating a surface that promotes bone fusion. The trigger 110 or other actuation mechanism can then be actuated to deliver bone graft material through the tube 120 lumen and openings 132 in the tip 130 to promote fusion of the bone.

Although use of the device 100 has been described with respect to an example spinal procedure, the device 100 can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the invention are encompassed in the claim set listed below.

What is claimed is:

1. A bone graft delivery system, comprising:
    an elongate tube comprising a proximal end and a distal end; and
    a tip at a distal end of the tube, the tip having one or more openings configured to deliver the bone graft material to a desired location, wherein the tip includes a surface configured to decorticate bone extending proximally of the one or more openings, the tip being a single monolithically formed piece.

2. The system of claim 1, wherein the surface configured to decorticate bone comprises a rasping surface.

3. The system of claim 1, wherein the surface configured to decorticate bone comprises jagged edges.

4. The system of claim 1, wherein the tip is made of metal.

5. The system of claim 1, wherein the tip is made of a radiopaque material.

6. The system of claim 1, wherein the tip is made of a durable medical plastic.

7. The system of claim 1, wherein the tip is made of a composite material.

8. The system of claim 1, wherein the tip includes one or more radiopaque markers.

9. The system of claim 1, wherein the tip has a blunt end.

10. The system of claim 1, wherein the elongate tube is rigid.

11. The system of claim 1, wherein the elongate tube includes a permanent bend.

12. A method for delivering bone graft material to a surgical location, comprising:
    positioning a bone graft delivery device adjacent the surgical location, the bone graft delivery device comprising an elongate tube and a distal tip, wherein the distal tip has a rasping surface and at least one opening for delivering the bone graft material to the surgical location;
    decorticating bone with the rasping surface of the distal tip; and
    with the rasping surface at the distal tip of the bone graft delivery device, delivering bone graft material through the tube and out the at least one opening of the distal tip.

13. The method of claim 12, wherein the bone graft material comprises autogenous, cadaveric and/or synthetic material.

14. The method of claim 12, wherein the bone graft delivery device is positioned at the surgical location through a minimally invasive opening in a patient's skin.

15. The method of claim 12, wherein the bone graft delivery device is positioned adjacent the spine and the distal tip decorticates a portion of the spine.

16. The method of claim 12, wherein decorticating bone with the distal tip comprises rasping bone with jagged edges of the distal tip.

17. The method of claim 12, wherein decorticating bone with the rasping surface of distal tip comprises actuating the distal tip by mechanical, battery powered, electric, pneumatic, or another means of force.

* * * * *